US006937897B2

(12) United States Patent
Min et al.

(10) Patent No.: US 6,937,897 B2
(45) Date of Patent: Aug. 30, 2005

(54) ELECTRODE FOR HIS BUNDLE STIMULATION

(75) Inventors: Xiaoyi Min, Thousand Oaks, CA (US); Terrell M. Williams, Brooklyn Park, MN (US)

(73) Assignee: Medtronic, Inc., Minneapolis, MN (US)

(*) Notice: Subject to any disclaimer, the term of this patent is extended or adjusted under 35 U.S.C. 154(b) by 324 days.

(21) Appl. No.: 10/261,750

(22) Filed: Sep. 30, 2002

(65) Prior Publication Data

US 2004/0064176 A1 Apr. 1, 2004

(51) Int. Cl.[7] .................................................. A61N 1/00
(52) U.S. Cl. ............................................ 607/9; 607/127
(58) Field of Search .............................. 607/122–127, 607/119–131, 4–28

(56) References Cited

U.S. PATENT DOCUMENTS

| | | | |
|---|---|---|---|
| 4,106,512 A | | 8/1978 | Bisping |
| 4,217,913 A | | 8/1980 | Dutcher |
| 4,311,153 A | | 1/1982 | Smits |
| 4,355,646 A | | 10/1982 | Kallok et al. |
| 4,497,326 A | | 2/1985 | Curry |
| 4,643,201 A | * | 2/1987 | Stokes ........................ 607/122 |
| 4,882,777 A | | 11/1989 | Narula ........................ 604/281 |
| 4,886,074 A | | 12/1989 | Bisping |
| 5,246,014 A | | 9/1993 | Williams et al. |
| 5,342,414 A | | 8/1994 | Mehra |
| 5,584,873 A | | 12/1996 | Shoberg et al. |
| 5,683,447 A | | 11/1997 | Bush et al. |
| 5,769,881 A | | 6/1998 | Schroeppel et al. |
| 5,837,006 A | | 11/1998 | Ocel et al. |
| 5,984,015 A | | 11/1999 | Vieregge |
| 6,052,625 A | | 4/2000 | Marshall |
| 6,141,594 A | * | 10/2000 | Flynn et al. ................. 607/127 |
| 6,178,355 B1 | | 1/2001 | Williams et al. |
| 6,256,541 B1 | | 7/2001 | Heil et al. ................... 607/123 |
| 6,341,234 B1 | | 1/2002 | Thong et al. .................. 607/9 |
| 2002/0111663 A1 | | 8/2002 | Dahl et al. .................. 607/122 |
| 2003/0083727 A1 | | 5/2003 | Casavant et al. |

OTHER PUBLICATIONS

Karpawich, P.P. et al., "Altered Cardiac Histology Following Apical Right Ventricular Pacing in Patients with Congenital Atrioventricular Block," PACE, vol. 22(0), p. 1372–1377 (1999).

Kolettis, T.M. et al., "Improved Left Ventricular Relaxation During Short–Term Right Ventricular Outflow Tract Compared to Apical Pacing," CHEST, vol. 117, pp. 60–64 (2000).

Rosenqvist, M. et al., "The Effect of Ventricular Activation Sequence on Cardiac Performance During Pacing," PACE, vol. 19, p. 1279–1286 (1996).

Takagi, Y. et al., "Effects of Proximal Ventricular Septal Pacing on Hemodynamics and Ventricular Activation," PACE, vol. 22, p. 1777–1781 (1999).

* cited by examiner

Primary Examiner—Scott M. Getzow
(74) Attorney, Agent, or Firm—Girma Wolde-Michael; Michael C. Soldner

(57) ABSTRACT

An electrical lead equipped with cathode and anode active succession electrodes for positioning in the vicinity of the His bundle tissue. The lead includes a lead body for carrying conductors coupled between electrodes located at or near the distal lead end and a connector assembly located at the proximal lead end for connecting to an implantable pacemaker. The electrode is shaped, at the distal end, for positioning and attachment in the His bundle and branches thereof, cathode and anode electrodes co-extensive with the lead body. The cathode and anode electrodes may be helical screw-in type or equivalent electrodes adapted for secure fixation deep within the His bundle tissue or the tissue in the vicinity of the His bundle.

3 Claims, 9 Drawing Sheets

ELECTRODE FOR HIS BUNDLE STIMULATION

FIELD OF THE INVENTION

The present invention relates generally to medical electrical leads and particularly to a cardiac pacing lead for stimulating the His bundle.

BACKGROUND OF THE INVENTION

The frequency, pathway of conduction and rate of propagation of action potentials through the heart, which cause the heart to beat in an efficient manner, are controlled by specialized groups of cardiac cells which form the cardiac conduction system. This special conduction system includes the sinoatrial node (SA node), the atrial internodal tracts, the atrioventricular node (AV node), the His bundle, and the right and left bundle branches.

The SA node, located at the junction of the superior vena cava and right atrium, normally acts as the natural pacemaker, generating action potentials, which are conducted through the rest of the heart. When normal conduction pathways are intact, an action potential generated in the SA node is conducted through the atria and to the AV node via the atrial internodal tracts. The conduction through the AV nodal tissue is takes longer than through the atrial tissue, resulting in a delay between atrial contraction and the start of ventricular contraction.

The AV node, located in the central fibrous body, conducts the action potential to the His bundle, located under the annulus of the tricuspid valve. The His bundle splits into the left and right bundle branches, which are formed of specialized fibers called "Purkinje fibers." The Purkinje fibers rapidly conduct the action potential down the ventricular septum, spreading the depolarization wavefront quickly through the remaining ventricular myocardium, producing a coordinated contraction of the ventricular muscle mass.

Conduction abnormalities may cause slowed or disrupted conduction anywhere along this conduction pathway. For example, the SA node may not generate action potentials at a fast enough rate resulting in too slow of heart rate, or bradycardia. AV block may prevent conduction of the action potential from the atria to the ventricles. These and other conduction abnormalities may be treated by an external or implantable pacemaker.

Pacemakers are typically coupled to the heart via one or more leads, carrying one or more electrodes for stimulating the heart and for sensing the intrinsic electrical signals associated with a conducted action potential. Electrodes are commonly placed on the endocardial surface using a transvenous approach. For example a right ventricular lead may be advanced into the right ventricle and placed such that an electrode is positioned at or near the right ventricular apex. Low capture thresholds and stable lead positioning have made the right ventricular apex a preferred ventricular stimulation site.

However, ventricular pacing at the location of the right ventricular apex does not mimic the normal ventricular conduction pathway. Both experimental and clinical studies have shown that septal pacing can improve various indices of cardiac function compared to apical pacing. See, for example, Kolettis T M, et al., Chest, 2000; 117:60–64, Rosenquvist M., et al, PACE 1996;19:1279–86, and Takagi Y, et al., PACE 1999; 22:1777–81. Direct myocardial stimulation can cause remodeling of the ventricular myocardium, including myofibrilar disarray and local hypertrophy away from the electrode. See, for example, Karpawich P P et al., PACE. 1999; 22(0):1372–7.

The most normal physiological approach to pacing the ventricles when normal AV nodal conduction fails may be to deliver electrical stimulation pulses directly to the His bundle. Depolarization of the His bundle tissue may be conducted normally through the ventricular conduction pathway, down the left and right bundle branches and to the remainder of the ventricular myocardium. The resulting ventricular contraction, which is more rapid, resulting in a narrow QRS complex and a more vigorous, normal contraction, may produce a better-coordinated contraction for achieving efficient heart pumping action.

The His bundle, however, is surrounded by non-excitable tissue, normally resulting in unacceptably high thresholds for depolarizing, or "capturing" the His bundle tissue. The current field produced around a conventional unipolar or bipolar stimulation electrode may not effectively reach the relatively deep His bundle tissue or penetrate the surrounding non-excitable tissue. Increasing the stimulation energy in an attempt to capture the His bundle can result in capturing other surrounding, excitable tissue. Two leads could be placed adjacent each other near the His bundle so that the tip electrodes could be used as a bipolar pacing pair. However, placement of two leads would require longer surgical time, may not allow for controlled inter-electrode spacing and would increase the number of lead bodies running through a patient's veins. A medical lead is needed, therefore, for delivering stimulation pulses for effectively capturing the His bundle and thereby recruiting the normal ventricular conduction pathway for more physiological contraction dynamics and potentially improved hemodynamics during cardiac pacing.

SUMMARY OF THE INVENTION

The present invention is directed at providing a cardiac pacing lead designed for effectively stimulating the His bundle. The present invention is realized in an electrical lead equipped with cathode and anode active fixation electrodes that may be positioned in or near the His bundle tissue. The lead includes a lead body, which may be a multi-lumen lead body, for carrying conductors coupled between electrodes located at or near the distal lead end and a connector assembly located at the proximal lead end for connecting to an implantable pacemaker.

In one embodiment, the distal lead end is bifurcated such that cathode and anode electrodes are located on separate branches of the lead. The cathode and anode electrodes may be helical, "screw-in" type, electrodes such that they may be fixed deep within the His bundle tissue. The electrodes may be positioned at a desired interelectrode distance by separating the two branches. In one embodiment the branches are separated and positioned by first deploying the lead with a guide catheter and positioning the electrode on a first branch, retracting the guide catheter so that the branches may be separated, then advancing a stylet into the lumen of the second branch and positioning the second electrode at a desired location relative to the first electrode. In another embodiment, the desired interelectrode distance may be achieved by pre-forming the lead branches.

A His bundle pacing lead may also be equipped with sensing ring electrodes located on one or both of the branches carrying the pacing anode and cathode electrodes. Alternatively, one or more sensing ring electrodes may be located on the main lead body, proximal to the bifurcation of the lead.

In another embodiment, the cathode and anode electrodes for His bundle stimulation are positioned along a single lead body that is preformed in a generally "S" shape. The generally "S" shape allows each electrode to be positioned against the annulus of the tricuspid valve, adjacent the His bundle and then fixed in or near the His bundle tissue.

In yet another embodiment, a His bundle pacing lead may be constructed by assembling two small diameter leads, each having an active fixation tip electrode, and then inserting the two leads into the lumen of larger diameter tubing. The larger diameter tubing has a length that is somewhat shorter than the two small diameter leads such that the two small-diameter leads extend from the distal end of the tubing. The portion of the two small diameter leads extending from the large-diameter tubing may then be separated such that the electrodes located at the distal end of each lead may be positioned at a desired location a given distance from each other. At the proximal end, the connector assemblies of each small diameter lead extend from the larger diameter tubing so that one lead may be connected to a cathode terminal and the second lead may be connected to an anode terminal of a pacemaker.

A His bundle pacing lead and method for deploying such a lead, as provided by the present invention, is expected to provide a more natural conduction and synchronized contraction response during cardiac pacing that will be more beneficial to the patient than pacing at other cardiac sites. Direct myocardial stimulation, which can cause remodeling of the ventricular myocardium, including myofibrilar disarray and local hypertrophy away from the electrode, is avoided. Furthermore, aspects of the present invention allow His bundle pacing to be achieved at lower pacing energies by stimulating deep within tissue containing the His bundle. Optimal cathode and anode placement for His bundle pacing creates a current field that is spread within the excitable tissue of the His bundle rather than through the non-excitable tissue layer surrounding the His bundle. The optimal cathode and anode placement achieved using aspects of the present invention, therefore, is expected to efficiently depolarize the His bundle tissue resulting in a more favorable myocardial conduction and contraction pattern.

DETAILED DESCRIPTION OF THE INVENTION

Figure 1:
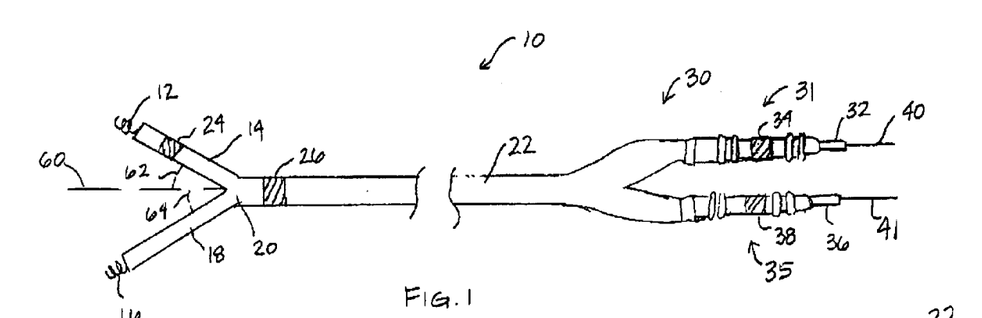
FIG. 1 is a plan view of one embodiment of a lead intended for stimulating the His bundle.

FIG. 1 is a plan view of one embodiment of a lead intended for stimulating the His bundle. Lead 10 is provided with a lead body 22 for carrying at least two conductors between electrodes, located at or near the distal end of lead 10, and corresponding connectors on a connector assembly 30 at the proximal end of the lead. Lead 10 is shown having a distal bifurcation 20 and two distal branches 14 and 18. Each branch 14 and 18 is provided with an active fixation member, shown as helices 12 and 16, that may be inserted into the central fibrous body in the vicinity of the His bundle. Helices 12 and 16 preferably serve as tip electrodes for use as a bipolar pacing electrode pair. Helices 12 and 16 may alternatively be provided as other types of active fixation electrodes, such as a barb or hook type electrode. Ring electrodes may optionally be provided for use in sensing cardiac signals and may be located on the main lead body 22 and/or branches 14 and 16, spaced proximally from helices 12 and 16. In FIG. 1, a ring electrode 24 is shown located on branch 14 and a ring electrode 26 is shown located on the main lead body 22.

Branch 14 extends at an angle 62 with respect to the main lead body central axis, indicated by dashed line 60. Branch 18 extends at an angle 64 with respect to axis 60. Angles 62 and 64 are shown to be approximately equal and each approximately 30 degrees, resulting in approximately a 60 degree angle between branches 14 and 18. Angles 62 and 64, however, may be any, preferably acute, angle which provides an appropriate distance between helices 12 and 16 for securing into His bundle stimulation sites. A preferable interelectrode distance for optimal His bundle stimulation is expected to be on the order of 4 to 10 mm. Branches 14 and 18 may also be curved so that helices 12 and 16 are presented to the tissue surface at a right angle rather than an oblique angle. Branches 14 and 18 may alternatively emerge from the main lead body 22 in parallel. The main lead body 22 and branches 14 and 18 are preferably formed from a resilient, biocompatible polymer such as polyurethane or silicone rubber. Bifurcation 20 and branches 14 and 18 may be preformed in a desired shape during molding processes.

A bifurcated proximal connector assembly 30 located at the proximal end of lead 10 is provided with a connector associated with each electrode. Connector assembly branch 31 includes a pin connector 32 corresponding to helix 12, and a ring connector 34 corresponding to ring electrode 24. Connector assembly branch 35 includes a pin connector 36 corresponding to helix 16 and a ring connector 28 corresponding to ring electrode 26. Stylets 40 and 41 are shown exiting pin connectors 32 and 36, respectively, and may be used to position the distal branches 14 and 18 at desired implant locations.

After implanting lead 10, connector assembly 30 may be connected to an implantable pacemaker having at least two connector ports. One pin connector may be connected to an anode terminal in the pacemaker connector block and the other pin connector may be connected to a cathode terminal in the pacemaker connector block such that the two helices serve as the anode-cathode pair during pacing. The ring connectors 34 and 38 may be coupled to ring terminals such that the ring electrodes 24 and 26 may be used, in combination with each other, one or both helices 12 and 16 or the pacemaker housing, for sensing cardiac signals or evoked responses.

Figures 2A, 2B, 2C:
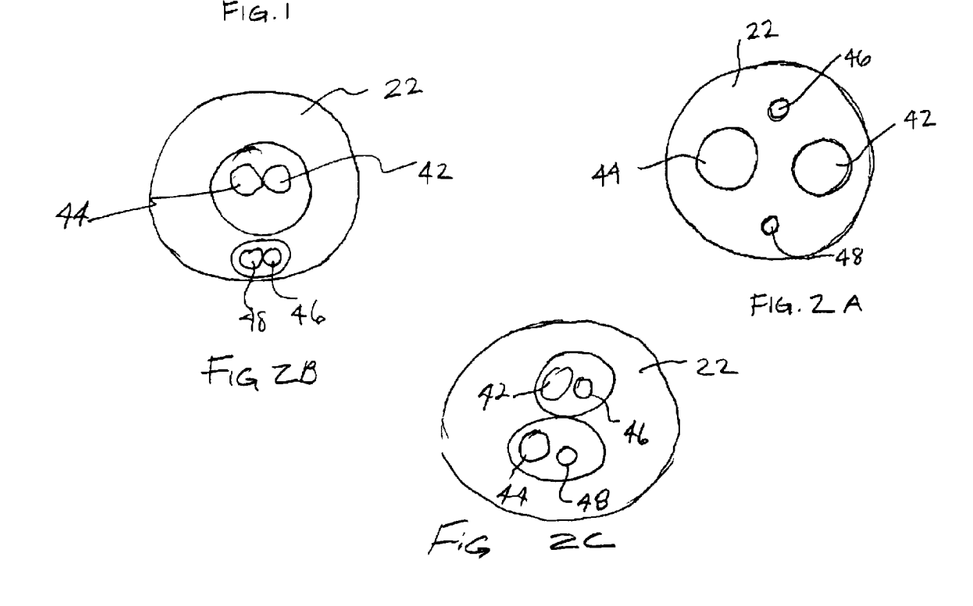
FIG. 2A is a cross-sectional view of the main lead body included in the lead of FIG. 1.
FIGS. 2B and 2C are alternate embodiments of FIG. 2A.

FIG. 2A is a cross-sectional view of the main lead body 22 of lead 10 in FIG. 1. Lead body 22 may be provided with multiple lumens for carrying multiple conductors between electrodes located at the distal lead end to the corresponding connectors at the proximal lead end. Lead body 22 may be provided as a multilumen lead body as generally described in U.S. Pat. No. 5,584,873 issued to Shoberg et al., incorporated herein by reference in its entirety. In FIG. 2, lead body 22 is shown having four lumens 42, 44, 46 and 48. Lumens 42 and 44 are provided for carrying separate conductors to helices 12 and 16. Lumens 46 and 48 are provided for carrying separate conductors to ring electrodes 24 and 26. Alternatively, the lead body 22 may be provided with two lumens for carrying conductors arranged concentrically, as disclosed in U.S. Pat. No. 4,355,646 issued to Kallok et al., also incorporated herein by reference in its entirety.

A multi-lumen lead body is shown in FIG. 2 to demonstrate the possibility of including one or more ring electrodes or other sensors on lead 10, in addition to helices 12 and 16. In a preferred embodiment including only helices 12 and 16, a bilumen lead body could be provided for carrying two conductors, one to each helix. If an optional ring electrode is included, two concentrically-arranged conductors could be provided extending through one lumen to one helix and the optional ring electrode and a third conductor may extend through a second lumen to the second helix.

FIG. 2B depicts an alternate configuration of lumens 42, 44 encased in a common lumen and set in adjacent placement therein. Similarly, conductor carrying lumens 48, 46 are encased in a common lumen.

FIG. 2C is yet another alternate embodiment in which lumen 42 and conductor lumen 46, and lumen 44 and conductor lumen 48 are encased in a common lumen, respectively.

Figure 3:
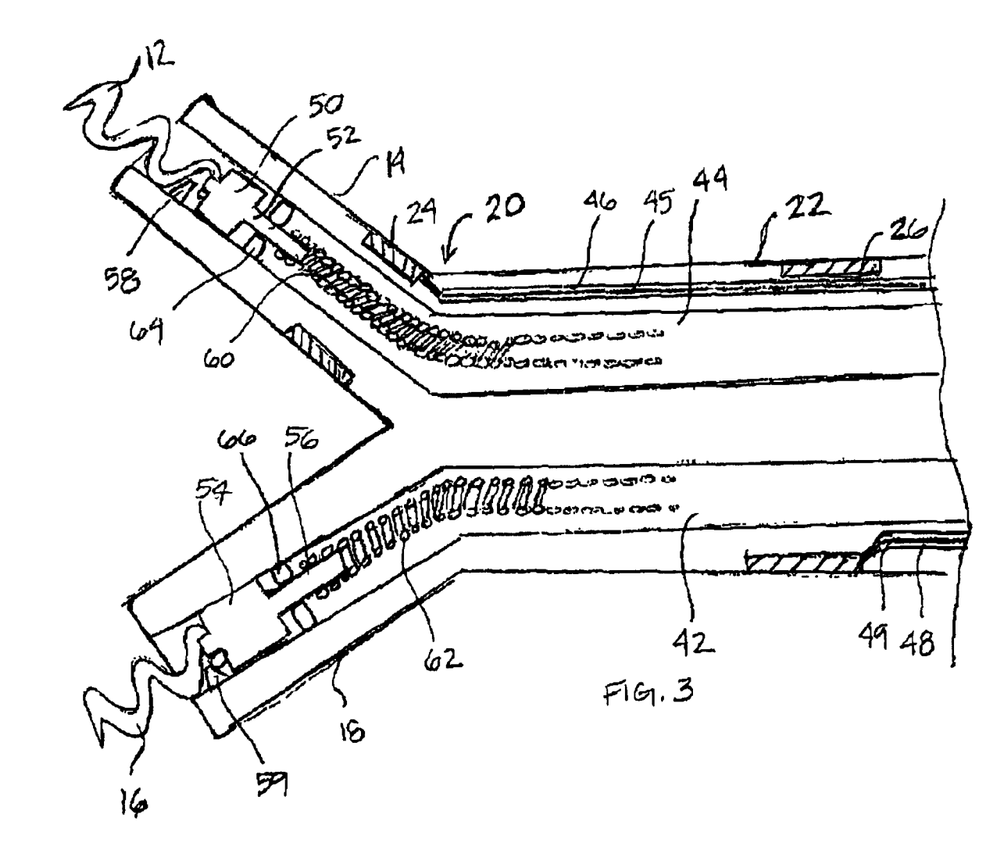
FIG. 3 is a side cut-away view of the distal branches of the lead shown in FIG. 1.

FIG. 3 is a side cut-away view of the distal branches of the lead 10 shown in FIG. 1. Helices 12 and 16 are preferably rotatable relative to lead body branches 14 and 18. A conductor 60, which is preferably a coiled conductor, extends through lumen 44 of main lead body 22 and continues into branch 14. Conductor 62 extends through lumen 42 of main lead body 22 and continues into branch 16.

Helix 12 is mounted on a drive shaft 50. Drive shaft 50 is provided with an electrically conductive stem 52. Conductor 60 is electrically and mechanically coupled to stem 52 at its distal end and to pin connector 32 (shown in FIG. 1) at its proximal end. Pin connector 32 may be rotated with respect to connector assembly 30 to cause rotation of coiled conductor 52 with respect to lead body 22. Rotation of coiled conductor 62 will cause advancement of helix 12 on guide 58. Similarly, helix 16, mounted on drive shaft 54 is advanced on guide 59 by rotating coiled conductor 62, which is coupled to drive shaft 54 via stem 56. A rotatable helix may be provided as generally described in U.S. Pat. No. 4,106,512 issued to Bisping, U.S. Pat. No. 4,886,074 to Bisping, and U.S. Pat. No. 5,837,006 to Ocel et al., all of which patents are incorporated herein by reference in their entirety.

Ring electrode 24 is coupled to a conductor 45 extending through lumen 46. Ring electrode 26 is coupled to a conductor 49 extending through lumen 48. Conductors 45 and 49 may be provided as cabled or stranded conductors. An example of a stranded conductor that may be used in the present invention is disclosed in U.S. Pat. No. 5,246,014 issued to Williams, et al., incorporated herein by reference in its entirety. Ring electrodes 24 and 26 may be used for sensing intrinsic cardiac signals or evoked responses for verifying capture following delivery of a pacing pulse.

Both helices 12 and 16 are shown in a partially extended position in FIG. 3. During implantation, both helices 12 and 16 are initially in a fully retracted position to prevent snagging or catching on anatomical structures as lead 10 is advanced through a venous pathway. Lead 10 may be advanced with the aid of a guide catheter or stylet. Once positioned at the final implant site, a first helix, for example helix 12, is advanced into a tissue site. The second branch 18 is then spaced a desired distance from the first branch 14 and the second helix 18 is advanced into a second tissue site.

In an alternative embodiment, a first helix may be fixedly attached at the distal end of a first lead branch, and a second helix may be rotatable with respect to a second lead branch, as will be further described below. Lead 10 may then be provided with an in-line connector assembly rather than a bifurcated connector assembly as shown in FIG. 1. The first helix, coupled via a conductor to a connector ring on an in-line connector assembly, may be screwed into a tissue site by rotating the main lead body at the proximal end while the second helix remains retracted within the distal branch. The second helix may be coupled via a conductor to connector pin of the in-line connector assembly. After fixing the first helix at a tissue site, the second helix may be advanced into a second, adjacent tissue site by rotating the connector pin.

Lead branches 14 and 18 may be provided with fluid-tight seals, 64 and 66, respectively, to prevent body fluids from entering lumens 42 and 44. Seals 64 and 66 may encircle a portion of the drive shaft, as generally disclosed in U.S. Pat. No. 5,984,015, issued to Hess, et al., incorporated herein by reference in its entirety. Alternatively, seals may be located at or near the distal end of the lead branches such that an advancing helix pierces through the seal as disclosed in U.S. Pat. No. 4,217,913 issued to Dutcher or U.S. Pat. No. 4,311,153, issued to Smits, both patents incorporated herein by reference in their entirety.

Figure 4:
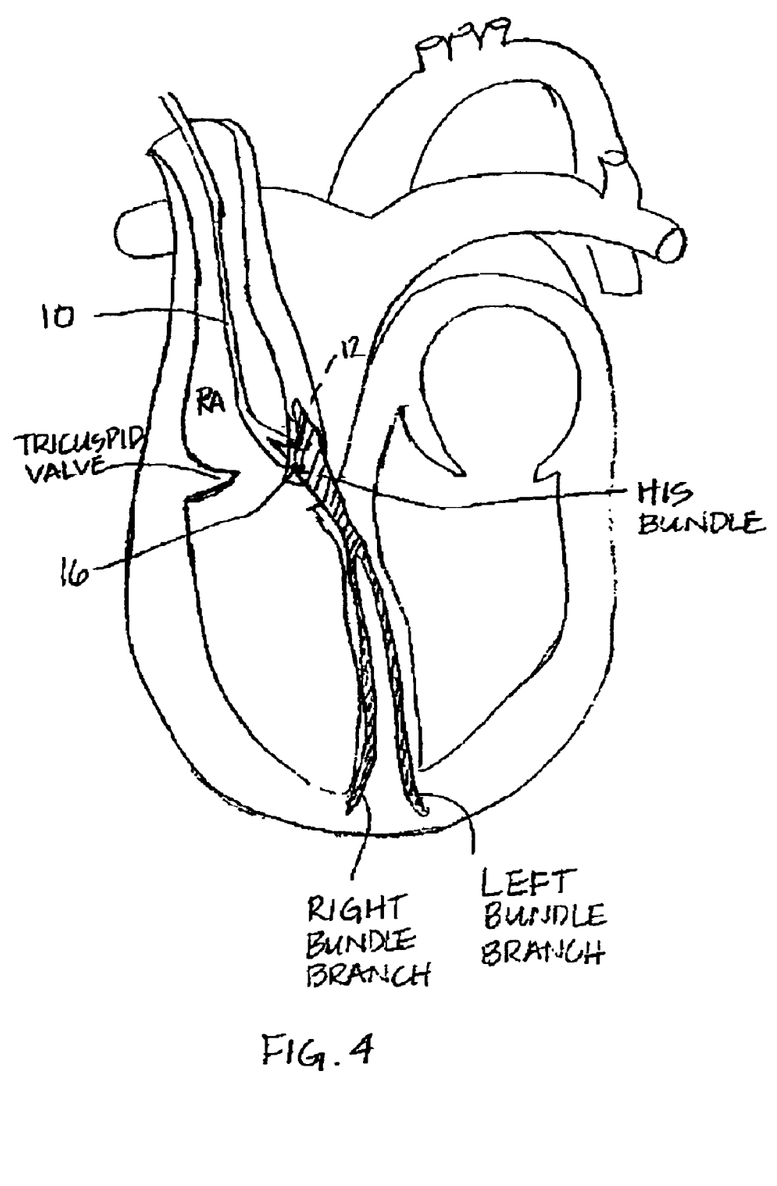
FIG. 4 is a partially cut-away view of the human heart illustrating the placement of the lead of FIG. 1 when it is used for stimulating the His bundle.

FIG. 4 is a partially cut-away view of the human heart illustrating the placement of lead 10 when it is used for stimulating the His bundle. The lead 10 is advanced into the right atrium (RA) to the annulus of the tricuspid valve, near the atrial septum where an intrinsic His potential can be mapped. Helices 12 and 16 are fixed in the central fibrous body, in close proximity, or preferably into, the His bundle. When a patient is diagnosed with a conduction abnormality superior to the His bundle, for example conduction abnormalities associated with the AV node, commonly referred to as "AV block," stimulation of the His bundle may produce more efficient ventricular contractions by recruiting the normal ventricular conduction pathways through the left and right bundle branches.

Figure 5A:
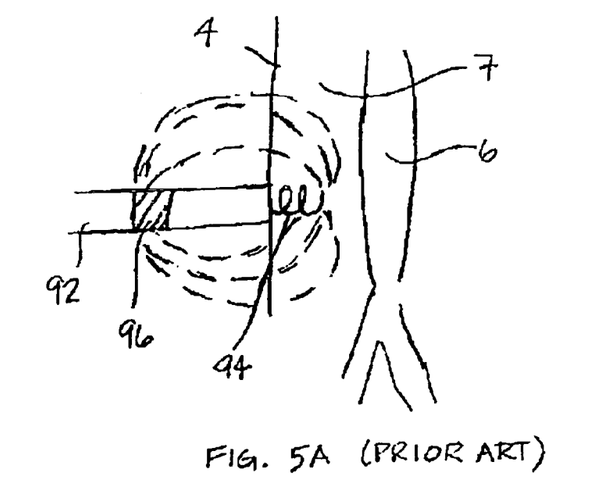
FIG. 5A is an illustration of the current field produced during bipolar stimulation using a conventional bipolar lead.

FIG. 5A is an illustration of the current field produced during bipolar stimulation using a conventional bipolar lead. A bipolar lead 92, having a helical tip electrode 94 and ring electrode 96 is shown implanted in the central fibrous body 4, over the His bundle 6. The His bundle is surrounded by fibrous, non-excitable tissue 7. The stimulating current field, indicated by dashed lines, will spread from the tip electrode 94 to the ring electrode 96. This current field is generally directed away from the His bundle tissue and may not even adequately penetrate the His bundle tissue to capture the cells. Higher pacing amplitude may produce a current field that penetrates the His bundle tissue, however other surrounding tissue may be captured and earlier depletion of the pacemaker battery becomes an issue.

Figure 5B:
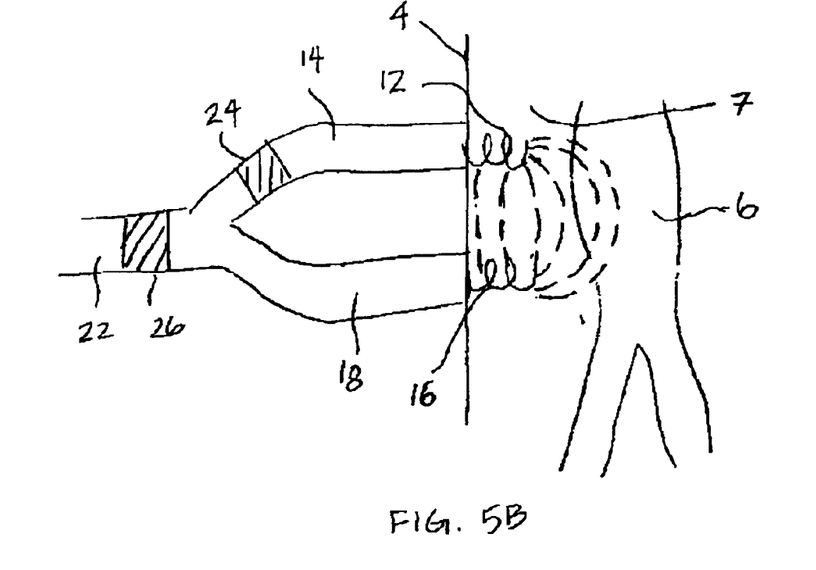
FIG. 5B is an illustration of the current field produced during bipolar stimulation using the branched lead shown in FIG. 1, in accordance with the present invention.

FIG. 5B is an illustration of the current field produced during bipolar stimulation using the bifurcated lead shown in FIG. 1, in accordance with the present invention. Helices 12 and 16 are implanted in the central fibrous body 4, over the His bundle 6. For a given pacing pulse energy, the current field, indicated by dashed lines, is expected to spread more deeply than the current field produced using the prior art lead shown in FIG. 5A. The current field is expected to pass through the fibrous, non-excitable tissue layer 7 and into the His bundle 6. An acceptable pacing pulse energy that does not excessively deplete battery charge may be used to effectively capture the His bundle and thereby recruit the normal ventricular conduction pathway, through the left and right bundle branches and Purkinje fiber system.

The depth of the current field produced will depend on the length of the helices, the distance between the two helices, and the delivered pulse energy. In some embodiments, the helices may be provided with insulation on a proximal portion of the helix such that the stimulating current field is generated from a distal portion of the helix creating a current field directed more exclusively toward the His bundle tissue. The active surface area of the distal, uninsulated portion of the helices must be large enough that it does not impede the stimulating current.

Figure 6:
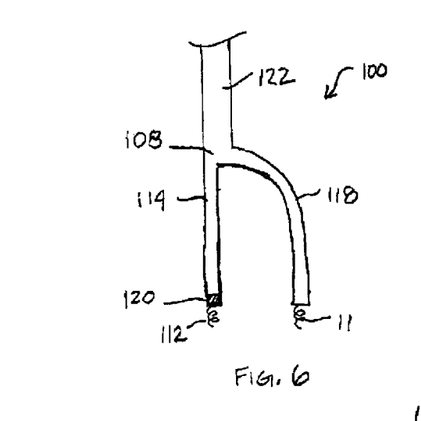
FIG. 6 is a plan view of the distal end of an alternative embodiment of a His bundle lead in accordance with the present invention.

FIG. 6 is a plan view of the distal end of an alternative embodiment of a His bundle lead in accordance with the present invention. In FIG. 6, one distal branch 114 extends linearly from the main lead body 122, and a second distal branch 118 extends at an angle, which may be approximately 90 degrees or less with respect to the main lead body 122. Branch 118 is curved so that distal fixation helix 116 may be aligned parallel to helix 112 against the central fibrous body over the His bundle. The branches of the lead 100 may be pre-shaped in a number of geometries wherein the branches 114 and 118 may be straight or having varying degrees of curvature and the branches may extend at varying angles from the bifurcation 108.

Branch 114 is shown having a tip ring electrode 120. In addition or alternatively to ring electrodes that are positioned more proximally on a lead branch or main lead body as shown on lead 10 of FIG. 1, a tip ring electrode may be provided on one or both branches and may be used for sensing intrinsic cardiac signals and/or evoked responses. Ring tip electrode 120 may resemble the electrode disclosed in U.S. Pat. No. 5,342,414 issued to Mehra, also incorporated herein by reference in its entirety.

Figure 7:
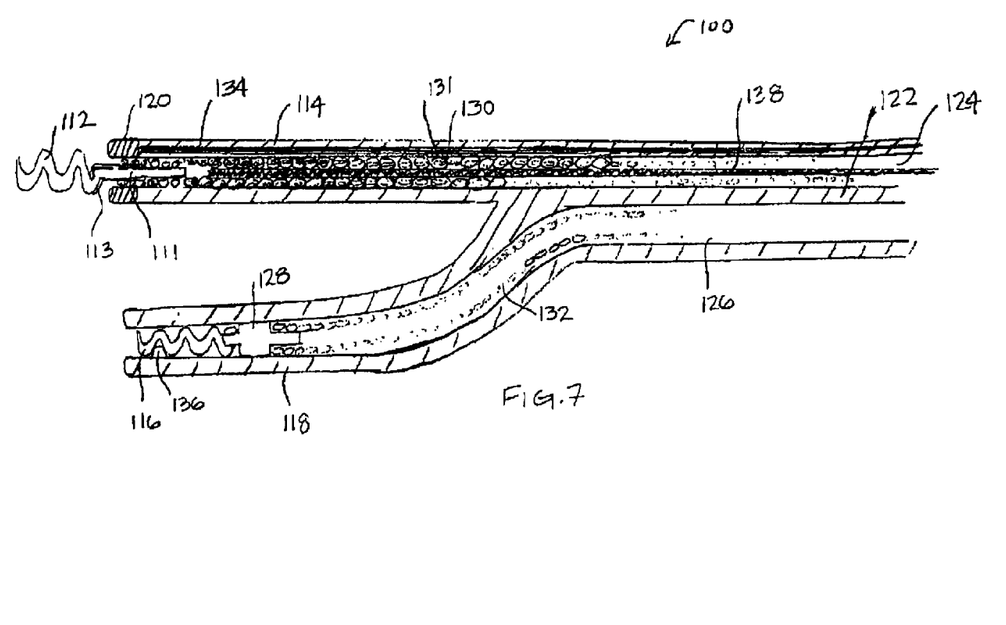
FIG. 7 is a side, cut-away view of the distal end of the lead of FIG. 6.

FIG. 7 is a side, cut-away view of the distal end of lead 100 of FIG. 6. Lead 100 is provided with one rotatable helix 116 and one non-rotatable helix 112. Helix 112 is provided with a conductive stem 111 that is electrically coupled to a conductor 130. Conductor 130 is preferably provided as a coiled conductor with insulation 131 to ensure electrical isolation between conductor 130 and tip ring electrode 120. Insulation 131 may be formed from an insulating polymer tubing, such as polytetrafluorethylene (PTFE) or ethylene tetraflouoretheylene (ETFE). Insulation 131 may be provided as generally described in U.S. Pat. No. 6,052,625 issued to Marshall, incorporated herein by reference in its entirety. Helix 112 may also be provided with an insulating coating 113 along a proximal segment of helix 112 to ensure electrical isolation between helix 112 and tip ring electrode 120. Tip ring electrode 120 is electrically coupled to a conductor 134, which may be provided as a coiled, cabled or stranded conductor.

In an alternative embodiment, helix 112 may serve only as a fixation device and tip ring electrode 120 may be used in combination with helix 116 for stimulating the His bundle tissue. In yet another embodiment, ring tip electrodes may be provided at the distal end of both lead branches and used as the pacing electrode pair with helices or other fixation members at the end of each lead branch used only for anchoring the branches. However, this embodiment may result in higher stimulation thresholds than embodiments that include at least one electrode inserted at a depth within the central fibrous body, in the vicinity of the His bundle.

A stylet 138 is shown extending through the lumen of coiled conductor 130 carried in lumen 124 of multi-lumen lead body 122. Stylet 138 may be used to aid in advancing lead 100 to a desired implant site, and positioning helix 112 over the His bundle. Lead body 122 may then be rotated at its proximal end to fix helix 112 in the central fibrous body, in or over the His bundle.

Helix 116 carried by distal branch 118 is mounted on drive shaft 128, which is further coupled to a coiled conductor 132 in a manner described previously in conjunction with FIG. 3. Helix 116 may be advanced into the central fibrous body, adjacent to helix 112, by rotating coiled conductor 132 at its proximal end. Helix 116 may be positioned at a desired distance from helix 112 with the use of a stylet advanced through lumen 126, down the center of coiled conductor 132. Branch 118 may also be preformed to naturally extend helix 116 a predetermined distance away from helix 112. Branch 118 could alternatively be provided with a shape memory material, such as Nitinol or a shape memory polymer, near its distal end that may be activated, by thermal or electric energy, to acquire a desired shape.

Lead 100 may alternatively be provided with a rotatable helix on branch 114 and a non-rotatable helix on curved branch 118. A guide catheter may be used for delivering lead 100 to an implant site. When branches 114 and 118 are contained within a guide catheter, curved branch 118, having a greater length than branch 114, may extend from the distal end of the guide catheter while branch 114 remains in the guide catheter. Lead 100 may be rotated to engage the non-rotatable helix on curved branch 118. The guide catheter could then be withdrawn to allow the distal end of branch 114 to be positioned against the central fibrous body such that the rotatable helix may be fixed in the vicinity of the His bundle.

Figure 8A:
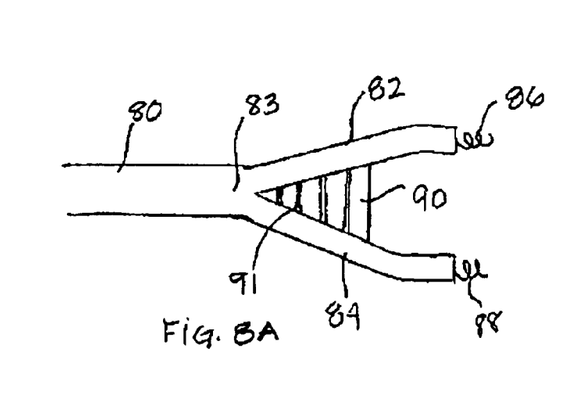
FIG. 8A is a plan view of an alternative embodiment of a branched lead in accordance with the present invention.

FIG. 8A is a plan view of an alternative embodiment of a branched lead in accordance with the present invention. In FIG. 8A, a separating membrane 90 is provided between two distal branches 82 and 84 extending from a bifurcation 83 of a main lead body 80. Membrane 90 maintains a desired distance between branches 82 and 84, thereby providing a desired interelectrode distance between helices 86 and 88. Membrane 90 may be provided as a thin, flexible member, formed from a biocompatible polymer such as polyurethane or silicone rubber, that may be ribbed or otherwise provided with relatively more rigid reinforcing structures 91 to aid in maintaining a desired distance between branches 82 and 84. Reinforcing structures 91 could also be provided as compressible structures that could be compressed to allow insertion into a guide catheter and would then expand when the guide catheter is removed to cause branches 82 and 84 to spread apart. Compressible reinforcing structures may fold or coil such that they do not produce too much friction between the lumen of the guide catheter and the distal branches 82 and 84, allowing the lead to still be easily passed through the guide catheter.

Figure 8B:
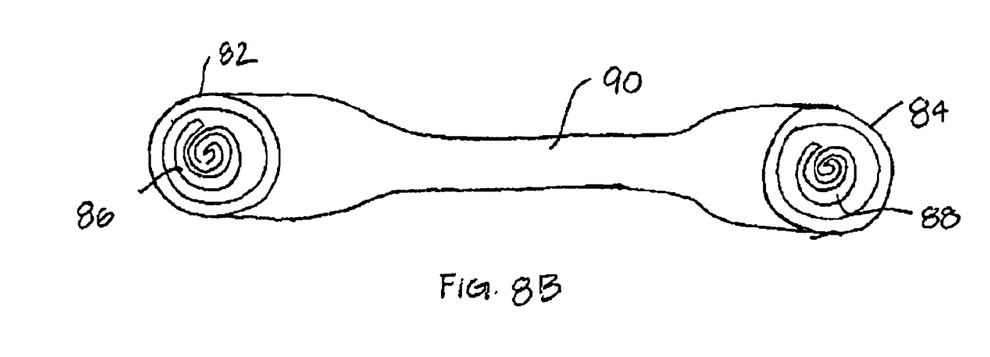
FIG. 8B is an end view of the lead shown in FIG. 8A.

FIG. 8B is an end view of the lead shown in FIG. 8A. Branches 82 and 84 are shown connected by membrane 90 extending between the two branches, holding the branches at a predetermined distance from each other. Membrane 90 is preferably flexible enough to be folded to allow the lead to be inserted into a guide catheter during a lead implant procedure. Upon withdrawing the guide catheter, membrane 90 will regain its natural shape, spreading branches 82 and 84 to a desired distance.

Figure 9:
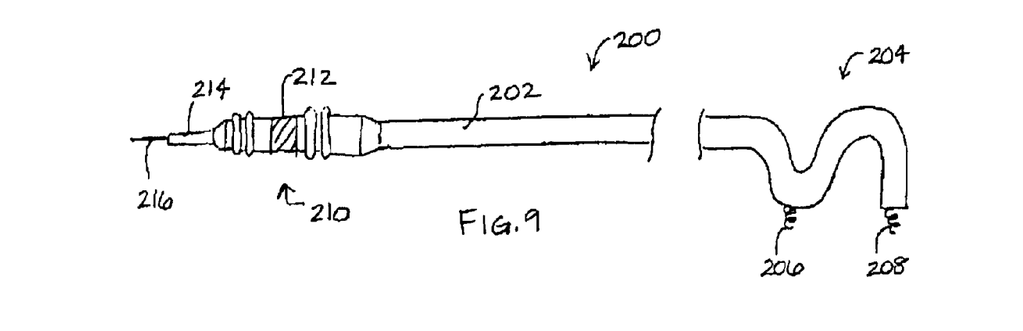
FIG. 9 is an alternative embodiment of a His bundle lead wherein the distal end of the lead is provided in a generally "S" shaped configuration.

FIG. 9 is an alternative embodiment of a His bundle lead wherein the distal end of the lead is provided in a generally "S" shaped configuration. Lead 200 includes a lead body 202 that is preformed into a general "S" shape at its distal end 204. A fixation member, shown as helix 206 extends from the first, more proximal, curve of the "S" shape. A second fixation member, shown as helix 208, extends from the distal lead end. Helices 206 and 208 are thus positioned such that they may be fixed adjacent to each other in the central fibrous body. The spacing between helices 206 and 208 is predetermined by the preformed shape of distal end 204.

One or more ring electrodes may optionally be provided in addition to helices 206 and 208. Ring electrodes may be located any where along the lead body 202, proximal to and/or in between helices 206 and 208. A ring tip electrode could also be included at the distal end of lead 200.

An in-line connector assembly 210 is provided at the proximal end of lead 200. Connector assembly 210 includes a pin connector 214 associated with helix 206 and a ring connector 212 associated with helix 208. A stylet 216 is shown entering the distal end of pin terminal 214.

Figure 10:
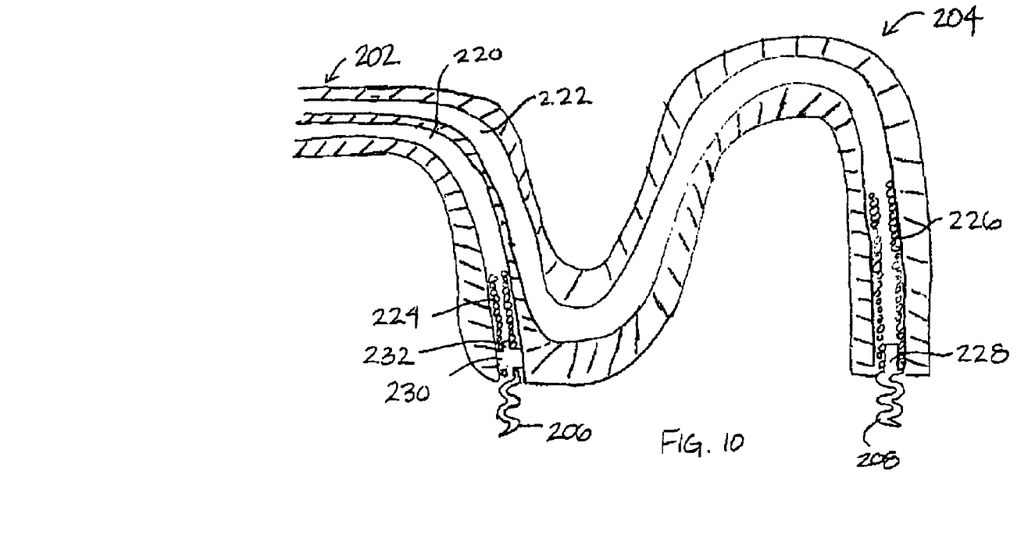
FIG. 10 is a side, cut-away view of the distal end of the lead of FIG. 9.

FIG. 10 is a side, cut-away view of the distal end 204 of lead 200 of FIG. 9. Lead body 202 is provided with at least two lumens 220 and 222 for carrying conductors 224 and 226 to helices 206 and 208, respectively. Helix 206 is preferably a rotatable helix, mounted on a drive shaft 230 having a conductive stem 232 coupled to coiled conductor 224. Rotation of coiled conductor 224 at its proximal end via pin terminal 214 will cause advancement of helix 206 in a manner as described previously. Helix 208 includes a conductive stem 228 which is electrically coupled to coiled conductor 226. Helix 208 is fixedly attached at the distal lead end 204. Helix 208 may alternatively be provided as a rotatable helix.

Figures 11A, 11B:
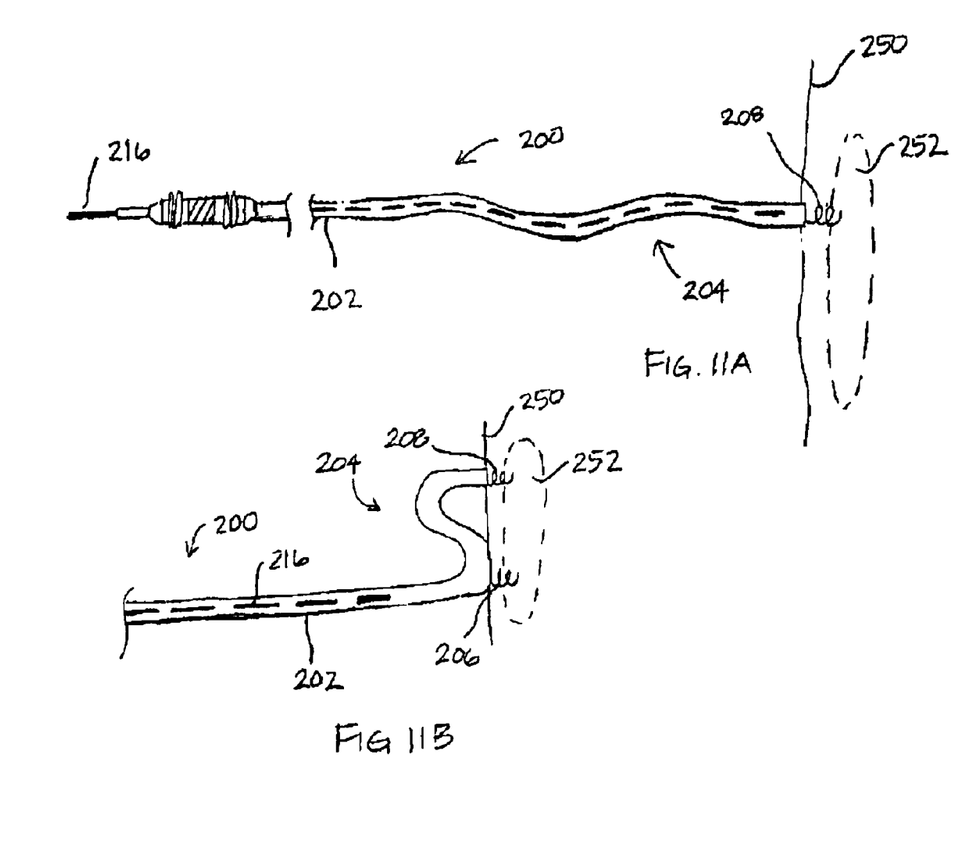
FIGS. 11A and 11B are plan views illustrating a method for implanting the lead of FIG. 9 using a stylet.

FIG. 11A is a plan view illustrating a method for implanting lead 200. A stiffening stylet 216, indicated by dashed line, may be advanced through lumen 222, through the center of coiled conductor 226 to distal lead end 204. Stylet 216 will straighten the preformed distal end 204 allowing lead 200 to be advanced easily through a venous pathway. The distal end of stylet 216 may be bent or curved to allow lead 200 to be maneuvered to the annulus of the tricuspid valve in a position over the His bundle 252. Lead 200 may be rotated, by rotating the proximal lead end, to secure helix 208 into the central fibrous body 250, in or over the His bundle 252.

In FIG. 11B, the stylet 216 has been withdrawn from the distal lead end 204. Withdrawal of stylet 216 allows the distal lead end 204 to regain its natural, generally "S" shape. Stylet 216 may be used to ensure helix 206 is positioned over the His bundle. The preformed shape of distal end 204 will determine the distance between helix 206 and helix 208. Helix 206 may then be advanced into the central fibrous body 250 by rotating the proximal end of conductor 224. Stylet 216 may then be fully withdrawn leaving lead 200 in place. Alternatively or additionally, a guide catheter may be used to aid in placing lead 200 over the His bundle.

Figure 12:
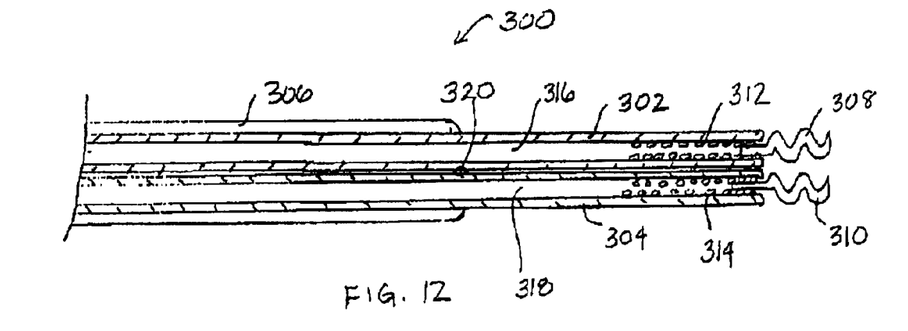
FIG. 12 is yet another embodiment of a branched lead according to the present invention wherein the branched lead is constructed by enclosing two, small diameter leads in a larger diameter tube.

FIG. 12 is yet another embodiment of a branched lead according to the present invention wherein the branched lead is constructed by enclosing two, small diameter leads in a larger diameter tube. Lead 300 includes two small diameter leads each equipped with active fixation electrodes, shown as helices 308 and 310, coupled to conductors 312 and 314, respectively. Conductors 312 and 314 are preferably carried in insulating tubing 302 and 304, respectively. Insulating tubes 302 and 304 are preferably constructed as thin-walled, flexible, biocompatible polymeric tubes formed, for example, from silicone rubber, polyurethane, PTFE, or ETFE. Conductors 312 and 314 are preferably coiled conductors such that a stylet may be advanced through lumens 316 and 318 to aid in implanting lead 300.

Insulating tubes 302 and 304 extend from an outer insulating tube 306. Tube 306 has a length somewhat shorter than tubes 302 and 304 such that tubes 302 and 304 extend out of tube 306 and may be parted to allow helices 308 and 310 to be implanted at a desired interelectrode distance. A distal seal 320, which may be formed by injecting a medical grade adhesive between insulating tubes 302 and 304, may be provided to seal the distal end of outer insulating tube 306.

Figure 13:
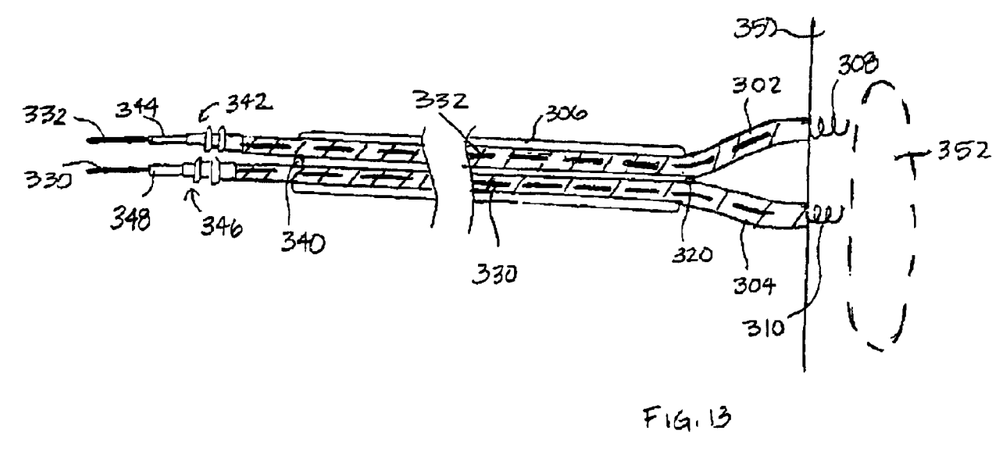
FIG. 13 is an illustration of the lead of FIG. 12 as it may be implanted for stimulating the His bundle.

FIG. 13 is an illustration of the lead of FIG. 12 as it may be fixed to the central fibrous body 350. The two small diameter leads are shown having proximal connector assemblies 342 and 346 exiting the outer insulating tube 306. A proximal seal 340, which may be provided by injecting a medical grade adhesive between proximal connector assemblies 342 and 346, may be provided to seal the proximal end of outer insulating tube 306. Pin connectors 344 and 348 allow the two small diameter leads to be connected to anode and cathode terminals of a pacemaker such that helices 308 and 310 may be used as an anode-cathode pair for pacing the His bundle 352. Stylets 330 and 332, indicated by dashed line, enter the hollow pin terminals 344 and 348 and are advanced within lumens 316 and 318 for use in positioning helices 308 and 310 at a desired distance from each other, against the central fibrous body 350, over the His bundle 352. Helices 308 and 310 may be provided as rotatable helices, as described previously, such that they may be advanced into the central fibrous body 350, into or over the His bundle 352, by rotating the proximal pin connectors 344 and 348.

Thus, a medical lead is provided for directing stimulating current more deeply into a targeted tissue site than conventional bipolar or unipolar pacing leads. While the various embodiments described herein are particularly suitable for delivering cardiac pacing pulses to the His bundle, various aspects of the present invention may be incorporated in medical leads used for other applications requiring delivery of a stimulation pulse at a depth within a targeted tissue. Numerous variations of the embodiments described herein may exist. The descriptions provided herein, therefore, should be considered exemplary and not limiting in regard to the following claims.

What is claimed is:

1. A method of stimulating the His bundle of a patient's heart comprising the steps of:
   providing a lead body having a proximal end with at least one connection assembly at the proximal end and having a bifurcated distal end with a first branch carrying an anode electrode and a second branch carrying a cathode electrode; and
   attaching the anode branch and the cathode branch to the His bundle at a desired interelectrode distance.

2. The method of claim 1 wherein the anode branch and the cathode branch are each attached by a helical, screw-in type anchoring device.

3. The method of claim 1, wherein the branches are attached by first deploying the lead with a guide catheter and positioning the electrode on the first branch, retracting the guide catheter, advancing a stylet into a lumen of the second branch and positioning the electrode on the second branch at a desired location relative to the first electrode.

* * * * *